(12) United States Patent
Haubold et al.

(10) Patent No.: US 6,275,286 B1
(45) Date of Patent: Aug. 14, 2001

(54) METHOD AND DEVICE FOR DETECTING FAULTS IN FLAT GLASS

(75) Inventors: Wolfgang Haubold, Bielefeld; Josef Droste, Glandorf; Edmund Paneff, Bielefeld, all of (DE)

(73) Assignee: Lasor AG (DE)

( * ) Notice: Subject to any disclaimer, the term of this patent is extended or adjusted under 35 U.S.C. 154(b) by 0 days.

(21) Appl. No.: 09/646,862
(22) PCT Filed: Mar. 24, 1999
(86) PCT No.: PCT/EP99/02110
  § 371 Date: Sep. 25, 2000
  § 102(e) Date: Sep. 25, 2000
(87) PCT Pub. No.: WO99/49303
  PCT Pub. Date: Sep. 30, 1999

(30) Foreign Application Priority Data

Mar. 25, 1998 (DE) .............................. 198 13 072

(51) Int. Cl.⁷ .................................................. G01N 21/00
(52) U.S. Cl. ..................... 356/239.1; 356/239.7; 356/239.8
(58) Field of Search ............................. 356/239.1, 239.2, 356/239.7, 239.8, 237.1–237.3; 250/562, 563, 548, 571, 572, 578, 559

(56) References Cited

U.S. PATENT DOCUMENTS 5,691,811 * 11/1997 Kibira ............................... 356/237.1

\* cited by examiner

*Primary Examiner*—Frank G. Font
*Assistant Examiner*—Michael P. Stafira
(74) *Attorney, Agent, or Firm*—Diller, Ramik & Wigh

(57) ABSTRACT

The invention relates to a method of determining the optical quality of and for detecting faults in flat glass, especially float glass, or other optically transparent materials, a video camera (1) being arranged to monitor an illuminating device (3) either through a glass (2) or by observing the reflection thereof on the glass or material, the focus being on the glass (2) and the material, respectively, and the video camera (1) generating signals in dependence on the quality of the glass (2), with these signals being evaluated, wherein an illuminating device (3) is used whose color and/or intensity is changed in a defined manner, the observation spot (6) of the video camera (1) in the faultless condition of the glass (2) is located substantially in the middle of the illuminating device (3), the illuminating device (3) has assigned thereto two video signals $U_1, U_2$, and a change of intensity of the video signals $U_1, U_2$ is used for evaluating the quality of the glass (2).

7 Claims, 3 Drawing Sheets

PRIOR ART

METHOD AND DEVICE FOR DETECTING FAULTS IN FLAT GLASS

BACKGROUND OF THE INVENTION

The invention relates to a method of determining the optical quality of and detecting faults in flat glass and other optically transparent materials.

A method is known for determining the optical quality of flat glass, especially of float glass, wherein a video camera is arranged to monitor an illuminating device either through the glass or by observing the reflection of the illuminating device on the glass. In this case, the focus of the video camera is on the glass and the sheet, respectively. In the process, the video camera generates signals in dependence on the quality of the glass. These signals will subsequently be evaluated.

FIG. 1 illustrates a method according to the state of the art. A video camera 1 or cell camera is provided to monitor, through a glass sheet 2, an illuminating device 3 having a dark field arranged thereon.

In case of a faultless material of the glass 2, the camera 1 will view the dark field 4. In case of a fault, the optical effect of the glass 2 will distort and/or deflect the field of view of the camera 1. If this effect is so large that the field of view of the camera 1 is caused to shift partially or wholly into the bright field 5, the video signal will undergo corresponding changes.

The dark field 4 must always be sufficiently large to prevent the field of view of the camera 1 from being shifted into the bright field 5 also due to vibration or bending (e.g. under the influence of temperature). For this purpose, the sensitivity of the system is limited by dead zones.

As long as the field of view deflected by a fault is located in the borderline region between the dark field 4 and the bright field 5, the amplitude of the error signal is dependent on the amount of the deflection. Since, however, the amplitude is also influenced by contamination of the sheet 2 under testing, a determination of the amount of the deflection is rendered impossible.

Faults in the glass usually have a core (bubble, inclusion). Since the core of a glass fault will primarily absorb light, a measuring of the core is possible only within the bright field 5. In the dark field 4, no measurement of the core is possible.

SUMMARY OF THE INVENTION

It is an object of the invention to provided a method wherein no dead zones exist and wherein the extent of the deflection (refractive power) and the size of the glass fault can be detected. Further, a possibility is to be provided to measure the cores of the faults in the glass.

According to the invention, the above object is achieved using illuminating devices whose color and/or intensity is changed in a defined manner from one outer edge to the other one, the observation spot of the video camera in the faultless condition of the glass is located substantially in the middle of the illuminating device, the illuminating device has assigned thereto two video signals $U_1, U_2$ according to color and/or intensity and a change of intensity of the video signals $U_1, U_2$ is used for evaluating the quality of the glass.

An advantageous variant is characterized in that the illuminating device comprises illuminating halves of different colors and that the video camera includes at least one color chip, with the video signals $U_1, U_2$ assigned respectively to one color.

Thus, the illuminating device comprises two colored halves (e.g. red/green). The video camera includes a color chip, with the video signals $U_1, U_2$ assigned to the two colors.

In the faultless condition of the sheet, the observation spot is located substantially in the middle of the illumination. The two voltages are substantially equal to each other. When, however, the observation spot is deflected or distorted due to optical deformation, one of the two voltages $U_1, U_2$ will be increased while the other one will be decreased.

Connecting of the two voltages to $$Upos = \frac{U_1 - U_2}{U_1 + U_2}$$

results in the voltage Upos, with its amplitude depending exclusively on the position of the observation spot of the camera. Alternatively, it is possible to use only the difference between the two video signals as a measure of the deflection and the position, respectively, of the observation spot.

In the above arrangement, no dead zones exist.

The amplitude of Upos is a measure of the strength of a deflection because of a fault.

A disturbance by contamination influences both of the voltages and is eliminated in the above term.

By application of $$U_h = U_1 + U_2,$$

a bright field is realized. By evaluating only negative signals of $U_h$, it is made possible to measure the core of the fault.

In the above described method, the enlargement of the illuminating spot through the depth of focus of the camera is utilized for the measurement of the positional change. In case of small apertures and large depths of focus, use can be made of graduated-density color filters.

$U_1$ and $U_2$ can be obtained also from a synchronous switching of the two illumination halves. To that end, the illumination is switched for each scan. $U_1$ and $U_2$ will then always be the video signals from the current scan and from the previous one. The illumination color can be chosen at random, and the camera used can be a BW camera.

In the evaluation, contamination is completely suppressed whereas deflections are maintained virtually unchanged.

BRIEF DESCRIPTION OF THE DRAWINGS

Further features of the invention are evident from the FIG. which will be described hereunder.

DESCRIPTION OF THE PREFERRED EMBODIMENTS

Figure 1:
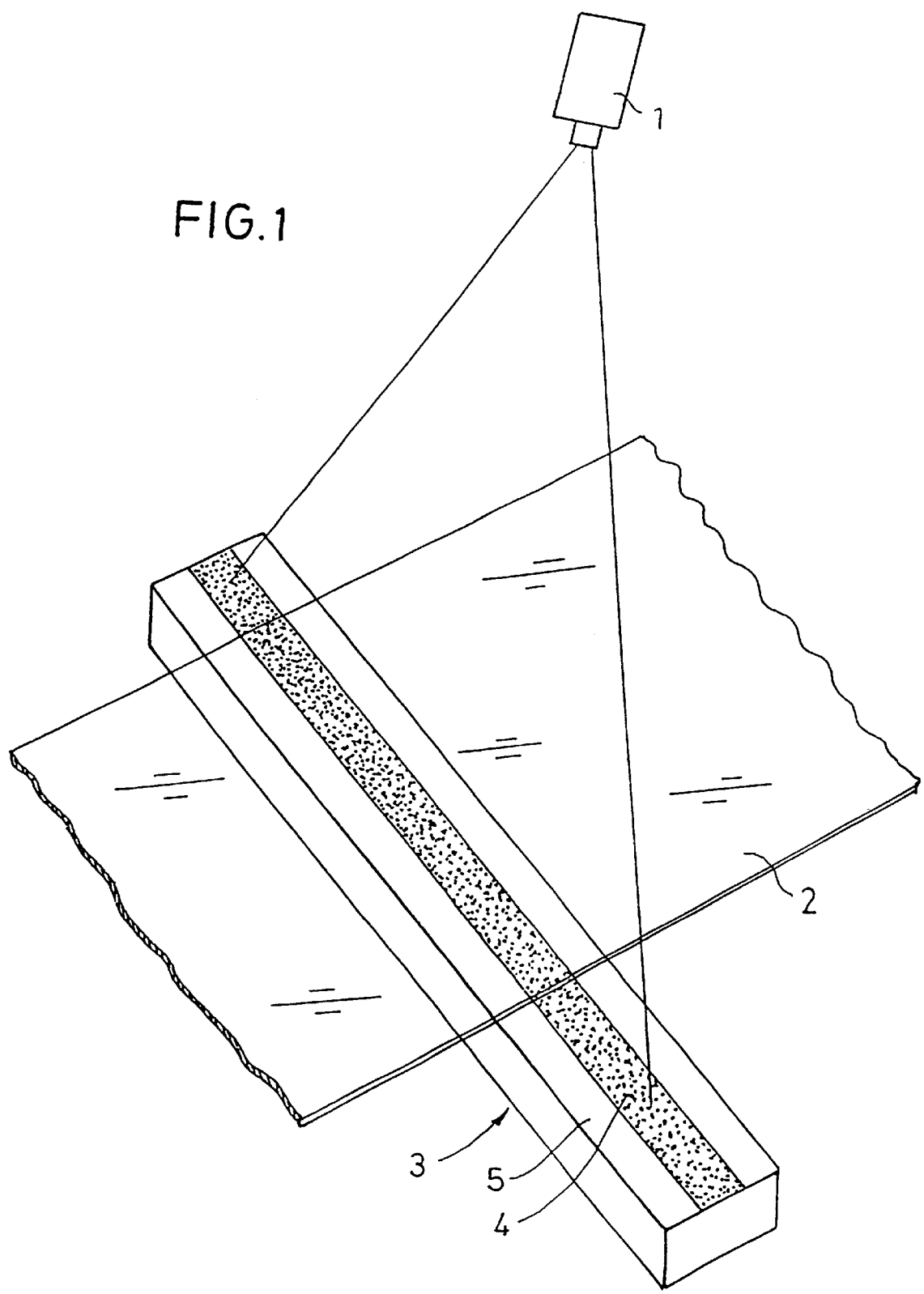
FIG. 1 is a fragmentary schematic perspective view, and illustrates a measuring method according to the prior art.

FIG. 1, illustrates a method for the detection of faults in flat glass according to the prior art.

The method involves a video camera 1, a glass sheet 2 and an illuminating device 3 comprising a dark field 4 and a bright field 5. Faults in the glass 2 will shift the observation spot of the video camera 1 from the dark field 4 into the bright field 5. This displacement is detected and evaluated.

Figure 2:
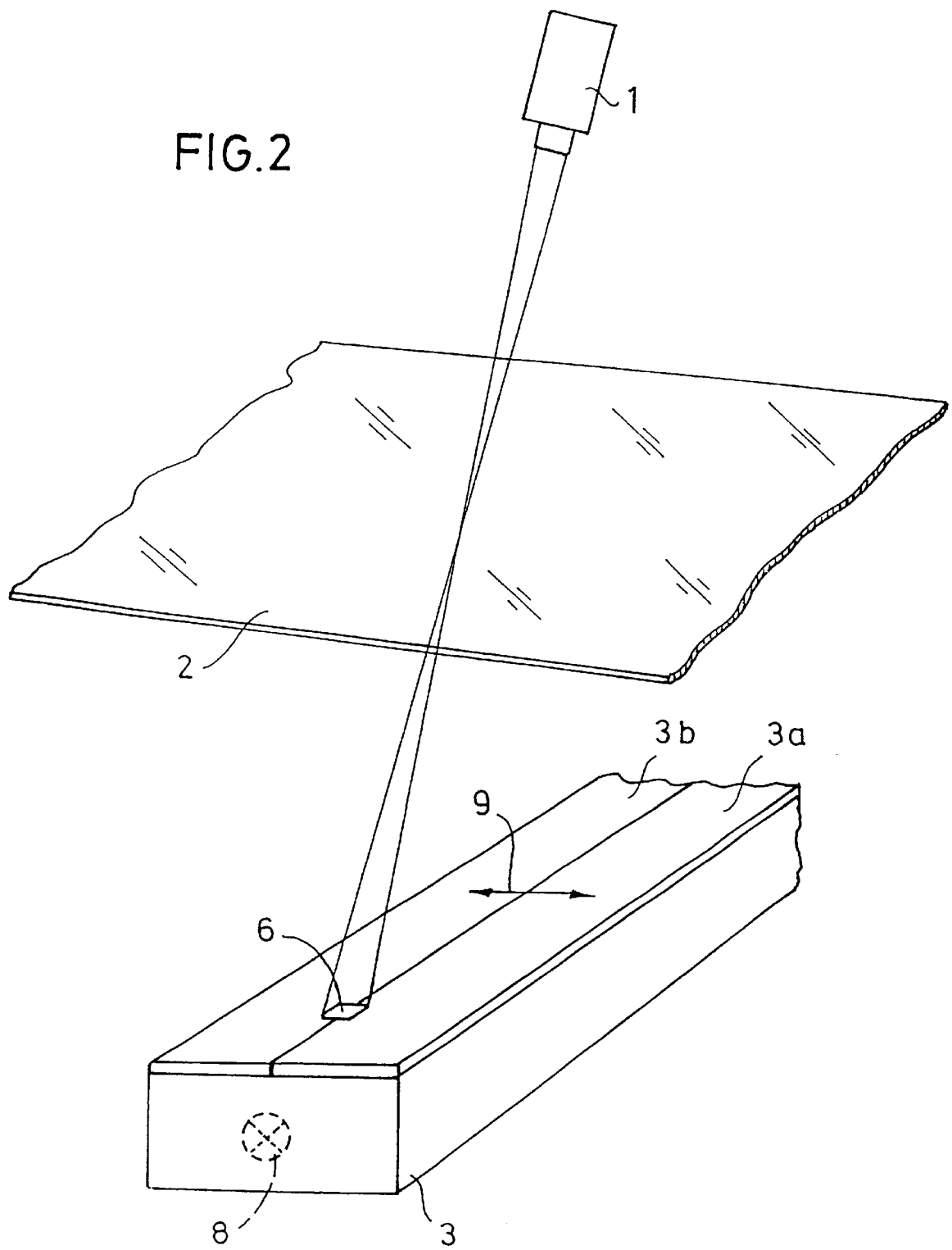
FIG. 2 is a fragmentary schematic perspective view, and illustrates the inventive method performed by using two colored illumination halves of the illuminating device.

FIG. 2 is a schematically illustrates a form of the inventive method performed using a video camera 1 arranged to view an illuminating device 3 through a glass sheet 2. In this configuration, the focus of video camera 1 is on the glass sheet 2.

The illuminating device 3 comprises two illumination halves 3a,3b having different colors; for instance, the illumination half 3a is red and illumination half 3b is green. Internally of the device, a lamp 8 is arranged, and the surface having the observation spot 6 of the video camera lying thereon is transparent. If the glass 2 is in a faultless condition, the observation spot 6 is located substantially in the middle between the two illumination halves 3a,3b.

Assigned to each illumination half 3a,3b, i.e. to each color, e.g. red and green, is a video signal $U_1,U_2$. In this connection, video camera 1 is provided with at least one color chip. In a faultless condition of glass 2, the two video signals $U_1,U_2$ are nearly equal in their intensity. Faults in the glass 2 will have the observation spot 6 shifted as indicated by the arrows 9 in FIG. 2. Thereby, one video signal becomes stronger and the other one weaker. This change will then be evaluated as explained in the introduction to the specification.

It is possible to use a plurality of cameras in combination so as to perform a complete examination of any desired widths with high resolution.

Figure 3:
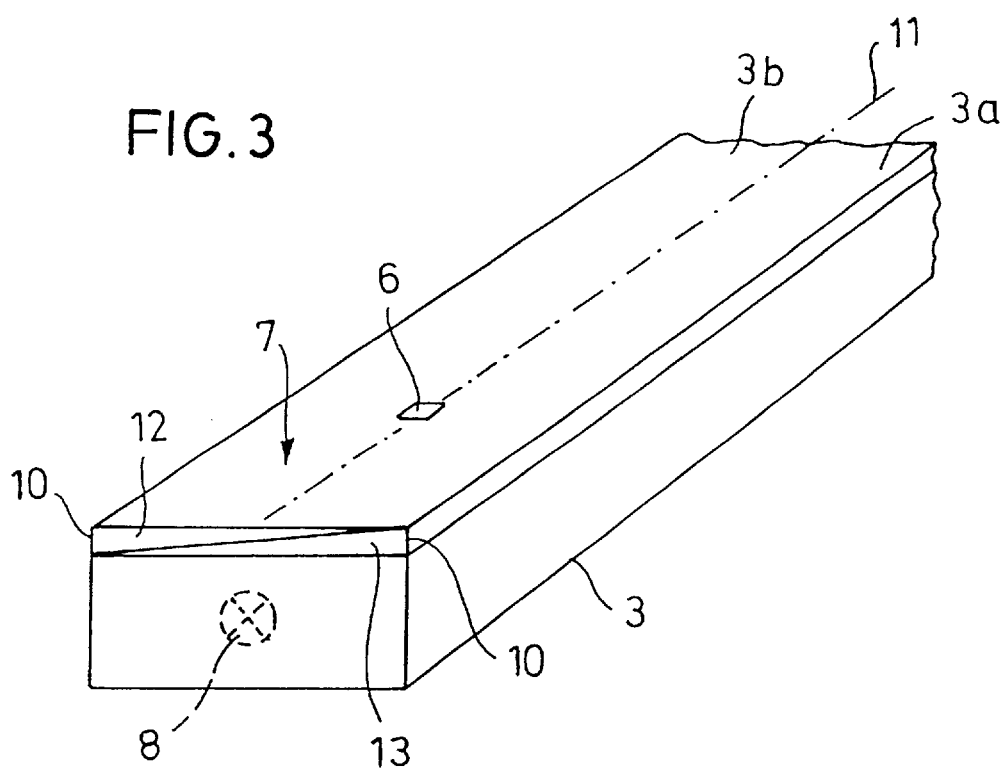
FIG. 3 is a fragmentary perspective view, and illustrates an illuminating device with a graduated-density color filter.

FIG. 3 is a schematic view of an illuminating device 3 comprising a light source or lamp 8 and a graduated-density color filter 7. In the illuminating device 3, the gradation of the color continuously decreases from the one outer edge 10a to the other outer edge 10b; by way of example, a red color gradation is outlined at 12 and a green color gradation is outlined at 13. Also here, the observation spot 6 of a video camera 1 (see FIG. 2) is located substantially in the middle 11 of the illuminating device 3. Again, a shifting of the observation spot 6 due to faults in the glass 2 (see FIG. 2) effects a change of the video signals $U_1,U_2$.

Figure 4:
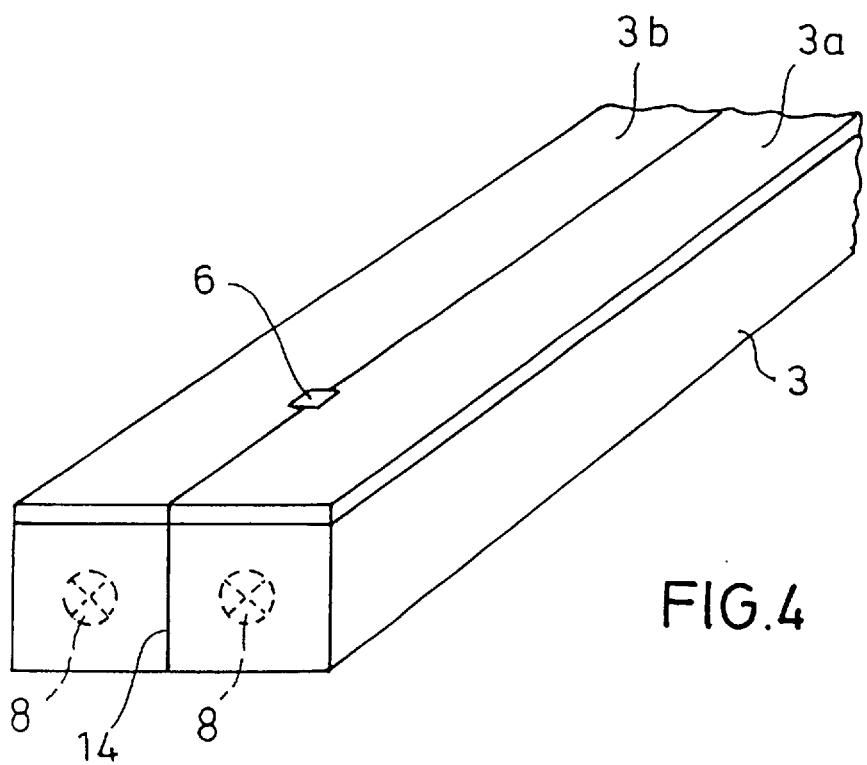
FIG. 4 is a fragmentary perspective view, and illustrates an illuminating device with alternating bright and dark fields.

FIG. 4 shows an illuminating device 3 with alternating bright and dark fields. For this arrangement, the illuminating device 3 is divided into two partial regions 3a,3b by a partition wall 14. The observation spot 6 of the video camera is arranged substantially in the middle between the two illumination halves 3a,3b. Each partial region has a lighting element 8 assigned thereto. The switching of the illumination halves 3a,3b is performed in synchronism with the line frequency of camera 1. Thus, video signals of substantial identical magnitude are obtained, irrespective of which one of the illumination halves 3a,3b is switched on. In case of a fault, the observation spot 6 is shifted. On the site of the fault, this shifting generates different influences on the signal amplitude, depending on which illumination half 3a,3b is presently active. Two successive lines constitute a signal pair $U_1,U_2$.

although a preferred embodiment of the invention has been specifically illustrated and described herein, it is to be understood that minor variations may be made in the apparatus without departing from the spirit and scope of the invention, as defined the appended claims.

What is claimed is:

1. A method of determining the optical quality of and detecting faults in flat glass, especially float glass, or other optically transparent materials, wherein a video camera (1) is arranged to monitor an illuminating device (3) either through the material (2) or by observing the reflection thereof on the material, the focus being on the glass and the material, respectively, and the video camera (1) generates signals in dependence on the quality of the glass (2) and these signals are evaluated, characterized in that an illuminating device (3) is used whose color and/or intensity is changed in a defined manner from one outer edge to the other one, that an observation spot (6) of the video camera (1) in the faultless condition of the glass (2) is located substantially in the middle of the illuminating device (3), that the illuminating device (3) has assigned thereto two video signals $U_1,U_2$ according to color and/or intensity and that a change of intensity of the video signals $U_1,U_2$ is used for evaluating the quality of the glass (2).

2. The method according to claim 1, characterized in that the illuminating device (3) comprises illumination halves (3a,3b) having different colors, and the video camera (1) includes at least one color chip, with the video signals $U_1,U_2$ being assigned respectively to one color.

3. The method according to claim 1, characterized in that the illuminating device (3) comprises a graduated-density color filters (7).

4. The method according to claim 1, characterized in that the illuminating device (3) comprises illumination halves (3a,3b) which are switched on and off alternately.

5. The method according to claim 1, characterized in that the difference between the two video signals $U_1,U_2$ is used as a measure of the deflection caused by the fault.

6. The method according to claim 5, characterized in that, as a measure of the deflection caused by the fault, use is made of the relation $$Upos = \frac{U_1 - U_2}{U_1 + U_2}$$

7. The method according to claim 1, characterized in that the measurement of a size of the core of the fault in the glass (2) is performed by use of a deviation from the maximum value of the addition of the video signals $U_1,U_2$, i.e. from $U_h = U_1 + U_2$.

* * * * *